US007115387B2

(12) United States Patent
Kanagaraj et al.

(10) Patent No.: US 7,115,387 B2
(45) Date of Patent: Oct. 3, 2006

(54) PROCESS FOR THE PREPARATION OF ALDEHYDE FROM A PROTEINOUS SOURCE FOR INDUSTRIAL APPLICATIONS

(75) Inventors: James Kanagaraj, Adayar (IN); Gopala Suseela Rajakumar, Adayar (IN); Sayeed Sadulla, Adayar (IN)

(73) Assignee: Council of Scientific & Industrial Research, New Delhi (IN)

( * ) Notice: Subject to any disclaimer, the term of this patent is extended or adjusted under 35 U.S.C. 154(b) by 367 days.

(21) Appl. No.: 10/662,620

(22) Filed: Sep. 15, 2003

(65) Prior Publication Data

US 2005/0059125 A1 Mar. 17, 2005

(51) Int. Cl.
*C12P 7/24* (2006.01)
*C14C 1/00* (2006.01)

(52) U.S. Cl. .................... 435/68.1; 8/94.15; 8/94.1 R; 8/94.19 R; 8/94.24; 435/147; 568/420; 568/423; 568/449; 568/451; 568/455

(58) Field of Classification Search ................ 435/147, 435/68.1; 8/94.15, 94.1 R, 94.19 R, 94.24; 568/420, 423, 449, 451, 455
See application file for complete search history.

(56) References Cited

U.S. PATENT DOCUMENTS 5,696,297 A * 12/1997 Kneuper et al. ............ 568/454

* cited by examiner

*Primary Examiner*—Herbert J. Lilling
(74) *Attorney, Agent, or Firm*—Schwegman, Lundberg, Woessner & Kluth P.A.

(57) ABSTRACT

A process is disclosed to treat the protein hydrolysate, prepared conventionally from a proteinous source, with alkyl halide to obtain alcohol which is subsequently oxidized to obtain aldehyde under certain specified conditions, thereby converting large protein molecules into aldehyde based industrial products of much smaller molecular size.

20 Claims, No Drawings

PROCESS FOR THE PREPARATION OF ALDEHYDE FROM A PROTEINOUS SOURCE FOR INDUSTRIAL APPLICATIONS

FIELD OF THE INVENTION

The present invention relates to a novel process for the preparation of aldehyde from a proteinous source for industrial applications. More particularly, the present invention relates to a process for the preparation of aldehyde of molecular weight in the range of 3000–5000 D. The aldehyde of the present invention has potential application in leather processing industry as a tanning agent to get softness, fullness, buffing property and lightweightness to the resulting leather. Moreover, the aldehyde thus obtained can also be used in photographic and carpentry industry.

BACKGROUND OF THE INVENTION

Aldehydes are compounds containing carbonyl group. When two hydrogens, or one hydrogen and one alkyl group are attached to the carbonyl the compound is an aldehyde. Aldehydes are syntheseised by oxidation of aliphatic alcohols of the general formula ROH, R being any alkyl group, whereby the alcohol is reacted with oxidizing agents like chromium (VI) oxide, potassium di chromate at a temperature not exceeding 40° C. The process results in the aldehydes of wide ranging molecular weights that may range between 10000–20000 D. This conventional process however requires that the reaction temperature have to be controlled to prevent the oxidation of generated aldehydes into carboxylic acids.

As reported by C. A. Buehler and D. E. Pearson (Survey of organic syntheses, Wiley-Interscience Publication, Chapter 10, 549,1970) aldehyde has been prepared from primary alcohol by using catalyst containing cobalt 5% and chromium 2%.

Also reported by C. A. Buehler and D. E. Pearson (Survey of organic syntheses, Wiley-Interscience Publication, Chapter 10, 549,1970) acetaldehyde has been prepared by three-step process, whereby glycerol is first reacted with acetone for projecting two of the hydroxyl groups followed by the oxidation of the resulting acetone glycerol over silver catalyst for 24 hours and subsequent hydrolysis of the product.

Thus aldehyde has conventionally been synthesized normally from non-proteinous source. It has been used for different industrial applications. Different aldehydes have been in use in the leather processing industry as tanning, retanning and even filling agent. The cost involved in the preparation of these chemicals from the conventional costly organic compounds poses a hindrance to the growth of the leather chemical industry involving aldehydes. Another limitation associated with these aldehydes is that some of the compounds, required for the preparation, have potential risk of being hazardous in respect of health and/or environment. Several attempts are therefore being made, in view of the growing concern for eco-sensitive scenario in the present age, to explore new sources for preparing aldehydes for application in different industries including that of leather processing. Several successful attempts have been made by different research groups to break down proteinous materials into the respective hydrolyzates.

Ramamurthy et al (Journal of society of leather technologists and chemists, 73,168,1985) provided a process for the preparation of keratin hydrolyzate, whereby a keratinous source is hydrolysed by 10% of alkali or acid or 0.25–0.5% of enzyme. The resulting product finds application in leather processing as syntan, filler and also as a chrome exhaust aid. The major limitation associated in this hydrolyzate is that the proteinous material itself is a limitation to its shelf life, which cannot go beyond 6 months.

Reference may be made to Kanagaraj et al (journal of American Leather Chemists Association, 97, 207–214, 2002) and our co-pending Indian Patent application No.210/DEL/2001, wherein a process has been provided for the preparation of protein based acrylic syntan, which has the wide application in leather processing. The syntan is prepared by hydrolyzing the protein source with acid or alkali followed by adjusting the pH to 6–7. The hydrolyzed protein source thus obtained is coplymerised with acrylates to obtain the acrylic syntan. The advantages of the acrylic syntan thus obtained are that it can be used as a filling agent, grain tightening agent and can withstand the temperature of 150° C. during glazing. The acrylic syntan increases the exhaustion of dye to the level of 80–90% in the resulting leather. But the limitation associated with the acrylic syntan is that it cannot be stored for more than 1 year. Moreover, the higher molecular weight of the syntan in the range of 15000–20000 D poses a problem in penetration. Another limitation associated with this is that it cannot be used as tanning agent because of the absence of any crosslinking agent and the tendency of the proteinous substance to decay. Thus both keratin hydrolyzate and protein based acrylic syntan cannot be used as self tanning agent.

Another copending Indian patent application No. 1063/DEL/2001 has provided a process for the preparation of novel proteinoid for industrial application which has the wide application in leather industry. The material is prepared by hydrolyzing a protein source with alkali and adjusting the pH of 6–7 and then subjected to oxidation by using organo-oxidizing agent to form reactive proteinoid. Here the molecular weight of the product is found to be as high as 7000–10000 D, hindering the penetration of the syntan into collagen fibres.

All these above attempts made on the proteinous source have thus been associated with a major limitation of partial break down of protein, resulting in the formation of significantly larger molecules, which are not suitable in leather processing. As reported by Herfield (Vegetable tannage, chapter 3, 3, 1986) the typical molecular weight of material that is suitable for tanning the pelt is in the range of 3000–5000 D.

OBJECTS OF THE PRESENT INVENTION

The main object of the present invention is to provide a novel process for the preparation of aldehyde from a proteinous source for industrial applications, which obviates the limitations as stated above.

Another object of the present invention is to provide a process for the preparation of aldehyde having molecular weight in the range of 3000–5000 D.

DETAILED DESCRIPTION OF THE PRESENT INVENTION

Accordingly, the present invention provides a novel process for the preparation of aldehyde from a proteinous source for industrial applications which comprises:

(i) subjecting the proteinous material to hydrolysis to obtain protein hydrolysate and sterilizing the protein hydrolysate to obtain sterilized protein hydrolysate, (ii) treating the sterilized protein hydrolysate, as formed in step (i), with 0.25–0.5% w/w of alkyl halide for a time period in the range of 20–30 minutes at a pH of 6–7 and adjusting the pH of the same in the range of 3–5 to obtain an alcohol containing slurry, (iii) reacting the alcohol containing slurry of step (ii), with 0.01–0.5% w/w, of an organo-oxidising agent at a temperature in the range of 20–35° C. followed by adjusting the pH of the resulting solution in the range of 5–7 to obtain an aldehyde containing solution, and (iv) separating the aldehyde containing solution, as formed in step (iii), to obtain aldehyde.

In an embodiment of the present invention, the proteinous material used is selected from fleshings, skin trimmings, keratin.

In another embodiment of the present invention, the proteinous material is hydrolyzed using alkali hydrolysis, acid hydrolysis, enzymatic hydrolysis.

In yet another embodiment of the present invention the hydrolyzed protein is sterilized using gamma radiation, ultraviolet radiation or autoclaving.

In still another embodiment of the present invention, organo-oxidising agent used may be selected from potassium permanganate, pyridinium chloro chromate, sodium hypochlorite.

In yet another embodiment of the present invention, the aldehyde containing solution is separated using dialysis, resin absorption or ion exchange.

The process of the present invention is described below in detail.

A proteinous material is hydrolysed by known method and the resulting hydrolysate is sterilized by conventional method. The sterilized protein hydrolyzate, formed thereby is treated with 0.25–0.5% w/w, of alkyl halide for a period of 20–30 minutes at a pH of 6–7. The pH of the resulting solution is adjusted in the range of 3–5 by known method, whereby alcohol is generated in the slurry. This slurry is treated with an oxidising agent at a temperature in the range of 20–35° C., whereby the pH is adjusted in the range of 5–7 by known method to obtain aldehyde mixture, which is subjected to conventional separation process to obtain aldehyde.

The inventive step of the present invention lies in the use of alkyl halide to convert protein hydrolysate into alcohol to facilitate subsequent preparation of aldehyde having molecular weight in the range of 3000–5000 D, by oxidation of alcohol, thereby suggesting an option for utilising proteinous wastes, which are of large molecular size, in the form of aldehyde based industrial products of much smaller molecular size.

The term large molecular size refers to molecules having molecular size greater than 100 KD and the term small molecular size refers molecules having molecular size lesser than 10 KD.

The following examples are given by way of illustration and therefore should not be construed to limit the scope of the present invention.

EXAMPLE 1

Dried and limed fleshing weighing lkg was taken in a vessel, washed with water to remove lime and other unwanted extraneous material. Then the material was delimed completely using 30 g of ammonium sulphate and was washed with 2 litres of plain waster. 2.5 g of alkaline protease was added to the washed material and hydrolysed at 55° C. After a period of 3 hours, the hydrolyzate was filtered and the pH of the filtrate material was found to be 9.0. 3 g of hydrochloric acid was added to the hydrolysed material and the pH was adjusted to 7. Then the material was sterilised by UV radiation for 10 minutes. The hydrolyzate was then subjected to reduction by using a mixture of 2.5 g sodium boro hydride for 20 minutes at 20° C. and the pH of the resulting solution is adjusted to 3 by known method to obtain a slurry containing alcohol.

0.1 g of potassium permanganate was then added to the slurry with continuous stirring, which was continued for a period of 20 minutes. The temperature was maintained at 20° C. The resulting slurry was subjected to test for aldehyde and it was found to be positive. The aldehyde containing mixture was then subjected to ion exchange separation. The pure aldehyde, obtained thereby was collected in a beaker and stored. The molecular weight of pure aldehyde found by Sodium Dodecyl Sulphate—Poly Acryl amide Gel Electrophoresis method was 3000 D.

The aldehyde was used for tanning of goat skin pelt at an offer of 10% based on pelt weight and the tanned leather was found to exhibit good softness.

EXAMPLE 2

Skin trimmings weighing 1 kg was taken in a vessel, washed with water to remove unwanted extraneous material. 100 g of sodium hydroxide was added to the washed material and hydrolysed. 2 g of hydrchloric acid was added to the hydrolysed material and the pH was adjusted to 7. Then the material was sterilised by gamma radiation for 20 minutes. The hydrolyzate was then subjected to reduction by using a mixture of 5.0 g sodium boro hydride for 30 minutes at 30° C. and the pH of the resulting solution is adjusted to 4 by known method to obtain a slurry containing alcohol.

0.5 g of sodium hypochlorite was then added to the slurry with continuous stirring, which was continued for a period of 30 minutes. The temperature was maintained at 35° C. The resulting slurry was subjected to test for aldehyde and it was found to be positive. The aldehyde mixture was then subjected to dialysis separation. The pure aldehyde, obtained thereby was collected in a beaker and stored. The molecular weight of pure aldehyde found out by Sodium Dodecyl Sulphate—Poly Acryl amide Gel Electrophoresis method was 4000 D.

The aldehyde was used for tanning of goat skin pelt at an offer of 10% based on pelt weight and the tanned leather was found to exhibit good softness.

EXAMPLE 3

Keratin weighing 1 kg was taken in a flask, washed with water to remove unwanted extraneous material. 100 g of hydro chloric acid was added to the washed material and hydrolysed. 10 g of sodium bicarbonate was added to the hydrolysed material and the pH was adjusted to 7. Then the material was sterilised by autoclave for 15 minutes. The hydrolyzate was then subjected to reduction by using a mixture of 4.0 g sodium boro hydride for 20 minutes at 25° C. and the pH of the resulting solution is adjusted to 5 by known method to obtain a slurry containing alcohol 0.5 g of pyridinium chloro chromate was then added to the slurry with continuous stirring, which was continued for a period of 20 minutes. The temperature was maintained at 25° C. The resulting slurry was subjected to test for aldehyde and it was found to be positive. The aldehyde mixture was then subjected to resin absorption separation. The pure aldehyde, obtained thereby was collected in a beaker and stored. The molecular weight of pure aldehyde found out by Sodium Dodecyl Sulphate—Poly Acryl amide Gel Electrophoresis method was 5000 D.

The aldehyde was used for tanning of goat skin pelt at an offer of 10% based on pelt weight and the tanned leather was found to exhibit good softness.

As mentioned above, the aldehyde obtained by following the process of the present invention has potential application as tanning agent in leather processing industry. The leather characteristics, as mentioned above are qualitative. These characteristics (softness, fullness, lightweightness, good napp property of suede leather etc.) are felt by experts in the area by physical touch. It is difficult to furnish objective data on this. The statements essentially refer to the observation that the product of the present invention is capable of resulting in leathers with those characteristics implying that the same finds application in leather industry.

ADVANTAGES OF THE PRESENT INVENTION

The main advantages of the present invention are as follows:

1. The process of the present invention is very simple and involves no difficult parameter.
2. The process is very economical.
3. The aldehyde prepared from the protein source can be stored for more than 1 year.
4. The aldehyde prepared is able to react with reactive groups of collagen and forms stable covalent cross-links.
5. The aldehyde gives improved exhaustion in the post tanning process.
6. The aldehyde gives lightweightness to the resulting leather.
7. The leather produced by this tanning agent ensures good napp property to the suede leather.
8. The tanning agent prepared can be used as self-tanning material, results in softness and fullness.

What is claimed is:

1. A process for preparing aldehyde having molecular weight in the range of 3000–5000 D from a proteinous material for industrial applications, said process comprising the steps of:

i) subjecting the proteinous material to hydrolysis to obtain protein hydrolysate and sterilizing the protein hydrolysate to obtain sterilized protein hydrolysate, ii) treating the sterilized protein hydrolysate, as formed in step (i), with 0.25–0.5% w/w of sodium borohydride for a time period in the range of 20–30 minutes at a pH of 6–7 and adjusting the pH of the same in the range of 3–5 to obtain an alcohol containing slurry, iii) reacting the alcohol containing slurry of step (ii), with 0.01–0.5% w/w, of an organo-oxidising agent at a temperature in the range of 20–35° C. followed by adjusting the pH of the resulting solution in the range of 5–7 to obtain an aldehyde containing solution; and iv) separating the aldehyde containing solution, as formed in step (iii), to obtain aldehyde.

2. The process as claimed in claim 1, wherein the proteinous material used is selected from fleshings, skin trimmings or keratin.

3. The process as claimed in claim 1 wherein in step (i), the proteinous material is hydrolyzed by alkali hydrolysis, acid hydrolysis or enzymatic hydrolysis.

4. The process as claimed in claim 1 wherein in step (i), the hydrolyzed protein material is sterilized using gamma radiation, ultraviolet radiation or autoclaving.

5. The process as claimed in claim 1 wherein in step (iii) the organo-oxidizing agent used is selected from potassium permanganate, pyridinium chloro chromate or sodium hypochlorite.

6. The process as claimed in claim 1 wherein in step (iv), the aldehyde containing solution is separated using dialysis, resin absorption or ion exchange.

7. The process as claimed in claim 1, wherein the aldehyde thus obtained can be stored for more than 1 year.

8. A process for preparing an aldehyde having a molecular weight of about 3000-5000 Daltons from a proteinous material, said process comprising the steps of:

i) subjecting the proteinous material to hydrolysis to obtain protein hydrolysate;

ii) treating the protein hydrolysate formed in step (i), with sodium borohydride at a pH of about 6-7 and adjusting the pH to about 3-5 to obtain an alcohol-containing slurry;

iii) reacting the alcohol-containing slurry of step (ii), with an organo-oxidizing agent followed by adjusting the pH of the resulting solution to about 5-7 to obtain an aldehyde- containing solution.

9. The process of claim 8, wherein the proteinous material used is derived from fleshings, skin trimmings, or keratin.

10. The process of claim 8 wherein in step (i), the proteinous material is hydrolyzed by alkali hydrolysis, acid hydrolysis, or enzymatic hydrolysis.

11. The process of claim 8 wherein in step (i), the protein hydrolysate is sterilized to provide sterilized protein hydrolysate.

12. The process of claim 11 wherein the hydrolyzed protein material is sterilized using gamma radiation, ultraviolet radiation, or autoclaving.

13. The process of claim 8 wherein in step (ii), about 0.25-0.5% w/w of sodium borohydride is employed.

14. The process of claim 8 wherein in step (ii), the protein hydrolysate is treated with sodium borohydride for about 20-30 minutes.

15. The process of claim 8 wherein in step (iii), about 0.01 to about 0.5% w/w, of the organo-oxidizing agent is employed.

16. The process of claim 8 wherein in step (iii) the organo-oxidizing agent is potassium permanganate, pyridinium chlorochromate, or sodium hypochlorite.

17. The process of claim 8 wherein in step (iii), the alcohol-containing slurry of step (ii) is contacted with the organo-oxidizing agent at a temperature of about 20° C to about 35° C.

18. The process of claim 8 wherein in the aldehyde is isolated from the aldehyde- containing solution of step (iii).

19. The process of claim 18 wherein the aldehyde is isolated from the aldehyde- containing solution using dialysis, resin absorption, or ion exchange.

20. The process of claim 19, wherein the aldehyde thus obtained is stable for more than about 1 year.

* * * * *